(12) United States Patent
Reed et al.

(10) Patent No.: US 9,072,564 B2
(45) Date of Patent: Jul. 7, 2015

(54) HAMMER TOE IMPLANT AND METHOD

(75) Inventors: Wesley Reed, Memphis, TN (US);
Dinesh V. Koka, Memphis, TN (US)

(73) Assignee: Wright Medical Technology, Inc.,
Memphis, TN (US)

( * ) Notice: Subject to any disclaimer, the term of this patent is extended or adjusted under 35 U.S.C. 154(b) by 8 days.

(21) Appl. No.: 13/086,136

(22) Filed: Apr. 13, 2011

(65) Prior Publication Data

US 2011/0301652 A1    Dec. 8, 2011

Related U.S. Application Data

(60) Provisional application No. 61/350,665, filed on Jun. 2, 2010.

(51) Int. Cl.
| | | |
|---|---|---|
| A61F 2/42 | (2006.01) |
| A61B 17/88 | (2006.01) |
| A61B 17/72 | (2006.01) |
| A61B 17/86 | (2006.01) |
| A61F 2/30 | (2006.01) |

(52) U.S. Cl.
CPC .......... *A61B 17/8891* (2013.01); *A61F 2/4225* (2013.01); *A61F 2002/4235* (2013.01); *A61F 2002/4228* (2013.01); *A61B 17/7291* (2013.01); *A61B 17/862* (2013.01); *A61B 17/8883* (2013.01); *A61F 2002/423* (2013.01); *A61F 2002/30622* (2013.01)

(58) Field of Classification Search
CPC ............... A61F 2002/4228; A61F 2002/423; A61F 2002/4238; A61F 2002/4243; A61F 2002/4246; A61F 2002/4248; A61F 2002/4251; A61F 2002/4253; A61F 2002/4256; A61F 2002/4258; A61F 2/4225
USPC ........ 623/21.19; 606/305; 411/388, 389, 402, 411/410
See application file for complete search history.

(56) References Cited

U.S. PATENT DOCUMENTS

| | | | | |
|---|---|---|---|---|
| 321,389 | A | * | 6/1885 | Schirmer ...................... 411/389 |
| 346,148 | A | * | 7/1886 | Durham ....................... 411/388 |
| 348,589 | A | | 9/1886 | Sloan |
| 373,074 | A | | 11/1887 | Jones |
| 430,236 | A | | 6/1890 | Rogers |
| 561,968 | A | | 6/1896 | Coulon |
| 736,121 | A | * | 8/1903 | Lipscomb ..................... 36/67 C |
| 821,025 | A | | 5/1906 | Davies |
| 1,966,835 | A | | 7/1934 | Stites |
| 2,140,749 | A | | 12/1938 | Kaplan |
| 2,361,107 | A | | 10/1944 | Johnson |
| 2,451,747 | A | * | 10/1948 | Kindt ............................ 164/249 |
| 2,600,517 | A | | 6/1952 | Rushing |
| 2,895,368 | A | | 7/1959 | Place |
| 3,466,669 | A | * | 9/1969 | Flatt ............................ 623/21.17 |
| 3,681,786 | A | | 8/1972 | Lynch |
| 4,156,296 | A | | 5/1979 | Johnson et al. |
| 4,204,284 | A | | 5/1980 | Koeneman |

(Continued)

FOREIGN PATENT DOCUMENTS

| | | |
|---|---|---|
| EP | 0340159 | 11/1989 |
| EP | 0409364 | 1/1991 |

(Continued)

*Primary Examiner* — David Bates
(74) *Attorney, Agent, or Firm* — Duane Morris LLP

(57) ABSTRACT

An implant is disclosed including an elongate threaded portion and a blade portion extending from the elongate threaded portion. The blade portion has a taper terminating at a point.

22 Claims, 19 Drawing Sheets

(56) References Cited

U.S. PATENT DOCUMENTS

| | | | |
|---|---|---|---|
| 4,213,208 A | 7/1980 | Marne | |
| 4,262,665 A | 4/1981 | Roalstad et al. | |
| 4,275,717 A | 6/1981 | Bolesky | |
| 4,276,660 A | 7/1981 | Laure | |
| 4,304,011 A | 12/1981 | Whelan, III | |
| 4,367,562 A | 1/1983 | Gauthier | |
| 4,516,569 A | 5/1985 | Evans et al. | |
| 4,590,928 A | 5/1986 | Hunt et al. | |
| 4,642,122 A | 2/1987 | Steffee | |
| 4,655,661 A | 4/1987 | Brandt | |
| 4,731,087 A | 3/1988 | Sculco et al. | |
| 4,865,606 A * | 9/1989 | Rehder | 623/20.23 |
| 4,908,031 A | 3/1990 | Frisch | |
| 4,932,974 A | 6/1990 | Pappas et al. | |
| 4,955,916 A | 9/1990 | Carignan et al. | |
| 4,963,144 A | 10/1990 | Huene | |
| 5,007,932 A | 4/1991 | Bekki et al. | |
| 5,037,440 A | 8/1991 | Koenig | |
| 5,047,059 A | 9/1991 | Saffar | |
| 5,092,896 A | 3/1992 | Meuli et al. | |
| 5,133,761 A | 7/1992 | Krouskop | |
| 5,147,363 A * | 9/1992 | Harle | 606/305 |
| 5,179,915 A | 1/1993 | Cohen et al. | |
| 5,199,839 A | 4/1993 | DeHaitre | |
| 5,207,712 A | 5/1993 | Cohen | |
| 5,326,366 A | 7/1994 | Pascarella et al. | |
| 5,330,476 A | 7/1994 | Hiot et al. | |
| 5,354,301 A | 10/1994 | Castellano | |
| 5,417,692 A | 5/1995 | Goble et al. | |
| 5,425,776 A | 6/1995 | Cohen | |
| 5,425,777 A | 6/1995 | Sarkisian et al. | |
| 5,458,648 A | 10/1995 | Berman et al. | |
| 5,480,447 A | 1/1996 | Skiba | |
| 5,484,443 A | 1/1996 | Pascarella et al. | |
| 5,498,265 A | 3/1996 | Asnis et al. | |
| 5,516,248 A | 5/1996 | DeHaitre | |
| 5,522,903 A | 6/1996 | Sokolow et al. | |
| 5,529,075 A | 6/1996 | Clark | |
| 5,595,563 A | 1/1997 | Moisdon | |
| 5,601,558 A | 2/1997 | Torrie et al. | |
| 5,634,925 A | 6/1997 | Urbanksi | |
| 5,669,913 A | 9/1997 | Zobel | |
| 5,674,297 A | 10/1997 | Lane et al. | |
| 5,683,466 A | 11/1997 | Vitale | |
| 5,713,904 A | 2/1998 | Errico et al. | |
| 5,725,585 A | 3/1998 | Zobel | |
| 5,776,202 A | 7/1998 | Copf et al. | |
| 5,919,193 A | 7/1999 | Slavitt | |
| 5,928,236 A * | 7/1999 | Augagneur et al. | 606/305 |
| 5,951,288 A | 9/1999 | Sawa | |
| 5,984,971 A | 11/1999 | Faccioli et al. | |
| 6,030,162 A | 2/2000 | Huebner | |
| 6,048,343 A | 4/2000 | Mathis et al. | |
| 6,099,571 A | 8/2000 | Knapp | |
| 6,102,642 A * | 8/2000 | Kawashita et al. | 411/401 |
| 6,200,345 B1 | 3/2001 | Morgan | |
| 6,248,109 B1 | 6/2001 | Stofella | |
| 6,319,284 B1 | 11/2001 | Rushdy et al. | |
| 6,352,560 B1 | 3/2002 | Poeschmann et al. | |
| 6,383,223 B1 | 5/2002 | Baehler et al. | |
| 6,386,877 B1 | 5/2002 | Sutter | |
| 6,413,260 B1 | 7/2002 | Berrevoets et al. | |
| 6,423,097 B2 | 7/2002 | Rauscher | |
| 6,454,808 B1 | 9/2002 | Masada | |
| 6,458,134 B1 | 10/2002 | Songer et al. | |
| 6,517,543 B1 | 2/2003 | Berrevoets et al. | |
| 6,551,343 B1 | 4/2003 | Törmälä et al. | |
| 6,679,668 B2 * | 1/2004 | Martin et al. | 411/388 |
| 7,041,106 B1 * | 5/2006 | Carver et al. | 606/309 |
| 7,192,445 B2 | 3/2007 | Ellingsen et al. | |
| 7,207,994 B2 | 4/2007 | Vlahos et al. | |
| 7,291,175 B1 | 11/2007 | Gordon | |
| 7,837,738 B2 | 11/2010 | Reigstad et al. | |
| 7,909,880 B1 | 3/2011 | Grant | |
| 8,262,712 B2 | 9/2012 | Coilard-Lavirotte et al. | |
| 8,616,091 B2 * | 12/2013 | Anderson | 81/52 |
| 8,636,457 B2 * | 1/2014 | Connors | 411/388 |
| 2001/0028836 A1 * | 10/2001 | Kohori | 411/402 |
| 2002/0072803 A1 | 6/2002 | Saunders et al. | |
| 2002/0111690 A1 | 8/2002 | Hyde | |
| 2003/0191422 A1 | 10/2003 | Sossong | |
| 2004/0097941 A1 | 5/2004 | Weiner et al. | |
| 2004/0220574 A1 * | 11/2004 | Pelo et al. | 606/73 |
| 2004/0230313 A1 | 11/2004 | Saunders | |
| 2005/0123672 A1 | 6/2005 | Justin et al. | |
| 2005/0187636 A1 | 8/2005 | Graham | |
| 2005/0283159 A1 | 12/2005 | Amara | |
| 2006/0074492 A1 | 4/2006 | Frey | |
| 2006/0100715 A1 | 5/2006 | De Villiers | |
| 2006/0129153 A1 | 6/2006 | Klaue et al. | |
| 2007/0078518 A1 | 4/2007 | Lavi | |
| 2007/0142920 A1 | 6/2007 | Niemi | |
| 2007/0177959 A1 * | 8/2007 | Chopp et al. | 411/389 |
| 2007/0213831 A1 | 9/2007 | de Cubber | |
| 2008/0051912 A1 | 2/2008 | Hollawell | |
| 2008/0086139 A1 | 4/2008 | Bourke et al. | |
| 2008/0195215 A1 | 8/2008 | Morton | |
| 2008/0221697 A1 | 9/2008 | Graser | |
| 2010/0061825 A1 * | 3/2010 | Liu et al. | 411/388 |
| 2010/0131072 A1 | 5/2010 | Schulte | |
| 2010/0185295 A1 | 7/2010 | Emmanuel | |
| 2010/0249942 A1 | 9/2010 | Goswami et al. | |
| 2010/0262254 A1 | 10/2010 | Lawrence et al. | |
| 2011/0004255 A1 | 1/2011 | Weiner et al. | |
| 2011/0082507 A1 | 4/2011 | Slaue | |
| 2011/0082508 A1 | 4/2011 | Reed | |
| 2011/0093085 A1 | 4/2011 | Morton | |
| 2011/0144644 A1 * | 6/2011 | Prandi et al. | 606/62 |
| 2011/0257652 A1 | 10/2011 | Roman | |
| 2011/0301652 A1 | 12/2011 | Reed et al. | |
| 2011/0301653 A1 | 12/2011 | Reed et al. | |
| 2012/0065692 A1 | 3/2012 | Champagne et al. | |

FOREIGN PATENT DOCUMENTS

| | | |
|---|---|---|
| EP | 0611557 | 8/1994 |
| FR | 736058 | 11/1932 |
| FR | 1036978 | 9/1953 |
| FR | 2605878 | 5/1988 |
| FR | 2645735 | 10/1990 |
| FR | 2651119 | 3/1991 |
| FR | 2783702 | 3/2000 |
| FR | 2787313 | 6/2000 |
| FR | 2794019 | 12/2000 |
| FR | 2846545 | 5/2004 |
| GB | 140983 | 4/1920 |
| GB | 2119655 | 11/1983 |
| GB | 2227540 | 1/1990 |
| GB | 2336415 | 10/1999 |
| GB | 2430625 | 4/2007 |
| WO | WO2006109004 | 10/2006 |

* cited by examiner

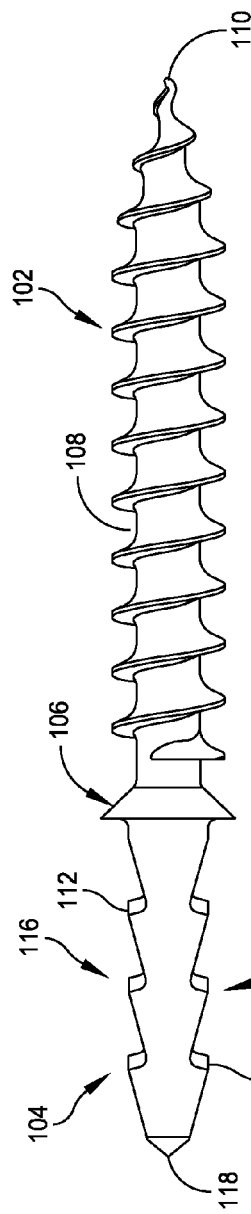
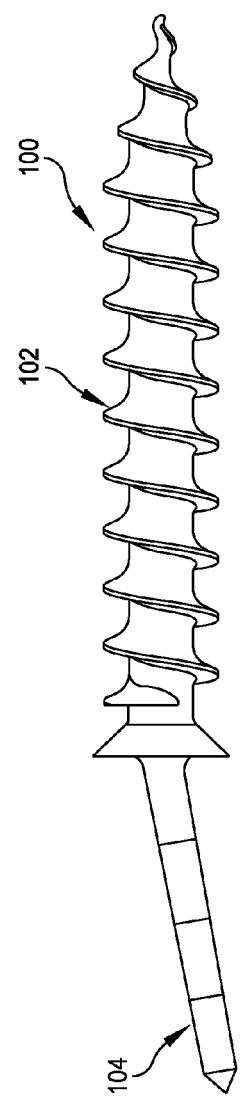
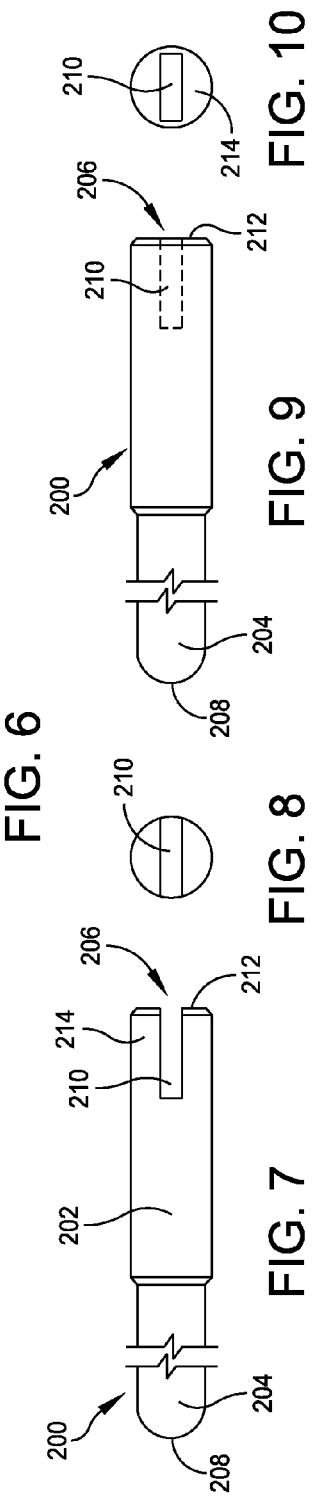
FIG. 5
FIG. 6
FIG. 7
FIG. 8
FIG. 9
FIG. 10
FIG. 11

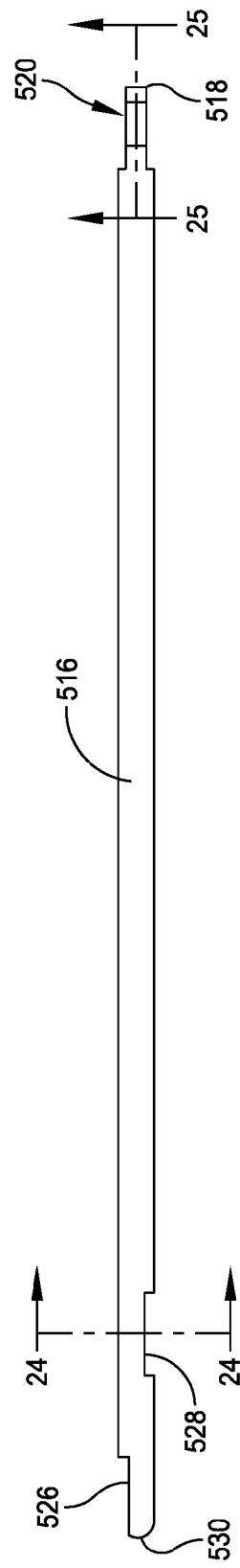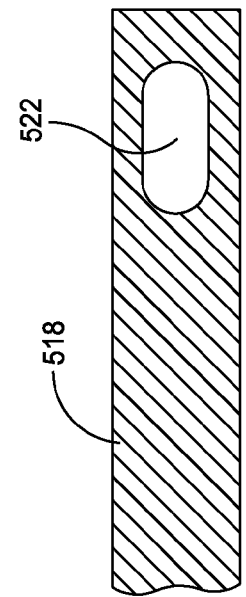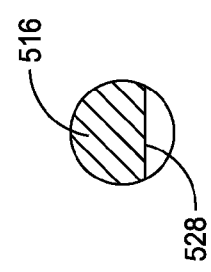
FIG. 23
FIG. 25
FIG. 24

HAMMER TOE IMPLANT AND METHOD

CROSS-REFERENCE TO RELATED APPLICATIONS

This application claims priority to U.S. Provisional Patent Application Ser. No. 61/350,665, which was filed on Jun. 2, 2010, the entirety of which is herein incorporated by reference.

FIELD OF DISCLOSURE

The disclosed system and method relate implants. More specifically, the disclosed system and method relate to installing an implant for treating hammer toe.

BACKGROUND

Hammer toe is a deformity of the toe that affects the alignment of the bones adjacent to the proximal interphalangeal (PIP) joint. Hammer toe can cause pain and can lead to difficulty in walking or wearing shoes. A hammer toe can often result in an open sore or wound on the foot. In some instances, surgery may be required to correct the deformity by fusing one or both of the PIP and distal interphalangeal (DIP) joints.

The most common corrective surgery includes the placement of a pin or rod in the distal, middle, and proximal phalanxes of the foot to fuse the PIP and DIP joints. The pin or rod is cut at the tip of the toe, externally of the body. A plastic or polymeric ball is placed over the exposed end of the rod, which remains in the foot of the patient until the PIP and/or DIP joints are fused in approximately 6 to 12 weeks. This conventional treatment has several drawbacks such as preventing the patient from wearing closed toe shoes while the rod or pin is in place, and the plastic or polymeric ball may snag a bed sheet or other object due to it extending from the tip of the toe resulting in substantial pain for the patient.

Another conventional implant includes a pair of threaded members that are disposed within adjacent bones of a patient's foot. The implants are then coupled to one another through male-female connection mechanism, which is difficult to install in situ and has a tendency to separate.

Yet another conventional implant has body including an oval head and a pair of feet, which are initially compressed. The implant is formed from nitinol and is refrigerated until it is ready to be installed. The head and feet of the implant expand due to the rising temperature of the implant to provide an outward force on the surrounding bone when installed. However, the temperature sensitive material may result in the implant deploying or expanding prior to being installed, which requires a new implant to be used.

Accordingly, an improved implant for treating hammer toe is desirable.

SUMMARY

An implant is disclosed including an elongate threaded portion and a blade portion extending from the elongate threaded portion. The blade portion has a taper terminating at a point.

A method is also disclosed in which an incision is formed to gain access to a joint between first and second bones. The first and second bones are flexed such that the bones are disposed at an angle from one another. A threaded portion of an implant is advanced into the first bone. The implant includes a blade portion extending from the elongate threaded portion. The second bone is repositioned such that a middle of the second bone is approximately aligned with the blade portion of the implant. The second bone is forced into engagement with the blade portion of the implant.

A surgical assembly is disclosed comprising an implant having an elongate body and a driving assembly. The implant includes a threaded end and a blade end extending from the threaded end. The blade end tapers along its thickness and its width to a point and includes a plurality of serrated edges. The driving assembly includes a handle, a driving rod extending from the handle, and an adapter coupled to an end of the driving rod. The adapter has a body defining a slot at one end that is sized and configured to receive the blade end of the implant.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein:

FIG. 5 is a side view of another example of a hammer toe implant;

FIG. 6 is a top side view of the hammer toe implant illustrated in FIG. 5;

FIG. 7 is a side view of one example of a driving adapter for use with the hammer toe implants illustrated in FIGS. 1 and 6;

FIG. 8 is an end view of the driving adapter illustrated in FIG. 7;

FIG. 9 is a side view of another example of a driving adapter for use with the hammer toe implants illustrated in FIGS. 1 and 6;

FIG. 10 is an end view of the driving adapter illustrated in FIG. 9;

FIG. 11 is an assembly view of a hammer toe implant engaged by a driving adapter;

FIG. 23 is a plan view of the driving rod of the driving assembly illustrated in FIG. 17;

FIG. 24 is a cross-sectional view of the driving rod taken along line 24-24 in FIG. 23;

FIG. 25 is a cross-sectional view of the fin of the driving rod taken along line 25-25 in FIG. 23;

DETAILED DESCRIPTION

Figure 1:
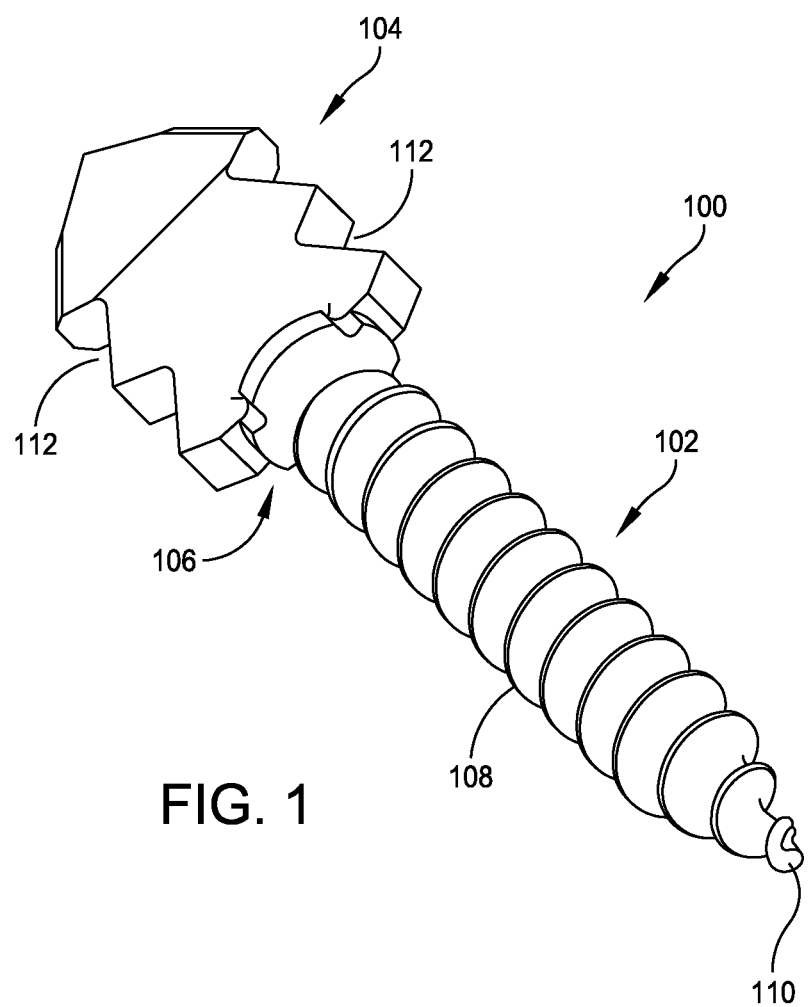
FIG. 1 is an isometric view of one example of an improved hammer toe implant.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

FIG. 1 illustrates one example of an improved implant 100 for treating hammer toe. As shown in FIG. 1, implant 100 includes a threaded portion 102 and a blade portion 104, which are connected together at an engagement portion 106. Implant 100 may have a substantially linear geometry having an overall length of approximately 19 mm (approximately 0.75 inches). In some embodiments, such as the one illustrated in FIGS. 5 and 6, blade portion 104 may be disposed at angle with respect to a longitudinal axis defined by the threaded portion 102. The angle may be between zero and 45 degrees, and more particularly between approximately five and fifteen degrees, although one skilled in the art will understand that implant 100 may have other dimensions and be provided in different sizes. For example, implant 100 may be provided in lengths of 16 mm and 22 mm, to name a few potential lengths.

Threaded portion 102 may include a plurality of threads 108 disposed along its entire length, which may be approximately 13 mm (approximately 0.5 inches). The tip 110 of threaded portion 102 may be pointed to facilitate the advancement of threads 108 into bone. Threads 108 may have a maximum outer diameter of approximately 2 mm (approximately 0.08 inches), although one skilled in the art will understand that thread portion 102 may have other dimensions and be configured to be received within a phalanx bone of a person. For example, threads may have an outer diameter of approximately 2.4 mm and 1.6 mm, to name a few potential possibilities.

Figure 2:
FIG. 2 is a top side view of the hammer toe implant illustrated in FIG. 1.
Figure 3:
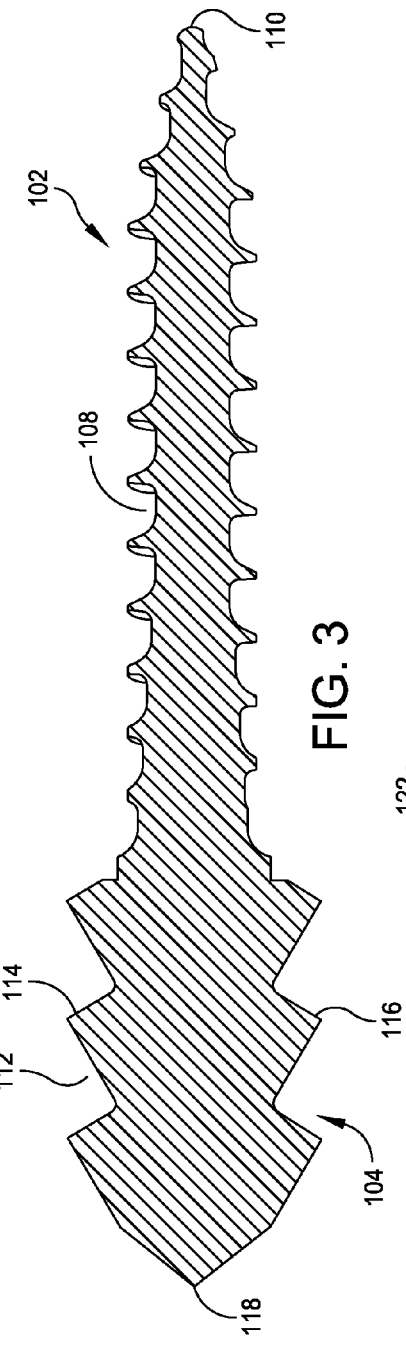
FIG. 3 is a sectional view of the hammer toe implant taken along line 3-3 in FIG. 2.
Figure 4:
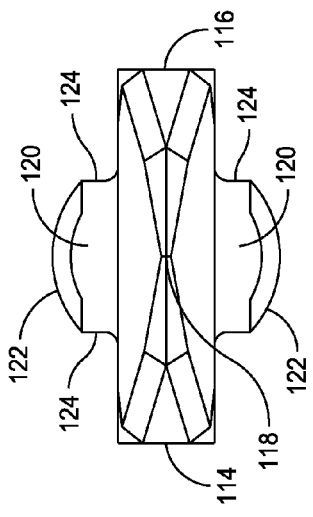
FIG. 4 is an end on view of the hammer toe implant taken along line 4-4 in FIG. 2.

As best seen in FIG. 3, blade portion 104 includes a plurality of serrated edges 112 on its top and bottom sides 114, 116. Blade portion 104 may have a width that is greater than its thickness as best seen in FIGS. 2 and 4. For example, blade portion 104 may have a width of approximately 0.4 centimeters (approximately 0.16 inches) and a thickness of approximately 0.1 centimeters (approximately 0.04 inches) each of which taper to point 118. Blade portion 104 may have a substantially rectangular cross-sectional area as illustrated in FIG. 4, although one skilled in the art will understand that blade portion 104 may have other cross-sectional geometries.

Engagement portion 106 may include a pair of protrusions 120 extending from opposite sides of implant 100 and having rounded outer edges 122. The sides 124 of protrusions 120 may be substantially parallel with each other as shown in FIG. 4.

Implant 100 is configured to be installed using a driving adapter 200 such as the one illustrated in FIGS. 7-10. The driving adapter 200 has an elongate body 202 having a proximal end 204 and a distal end 206. Body 202 of driving adapter 200 may have a circular cross-sectional geometry, although one skilled in the art will understand that body 202 may have other cross-sectional geometries including, but not limited to, triangular, rectangular, pentagonal, and hexagonal to name a few.

Proximal end 204 may be substantially solid and have a rounded tip 208. Distal end 206 may define a slot 210 sized and configured to receive blade portion 104 of implant 100 therein. Slot 210 may have a rectangular cross-sectional geometry and have a depth that is sufficient to receive the entire blade portion 104 of implant 100 such that distal edges 212 of slot 210 contact protrusions 120 of engagement portion 106. However, one skilled in the art will understand that slot 210 may have other cross-sectional geometries and dimensions. Slot 210 may extend through side walls 214 of body 202 as shown in FIGS. 7 and 8, or side walls 214 may completely enclose slot 210 as shown in FIGS. 9 and 10.

If the driving adapter 200 is to be used with an implant 100 having a substantially linear lengthwise geometry such as the implant 100 illustrated in FIGS. 1-5, then slot 210 may extend in a direction that is substantially parallel to an axis defined by body 202 of driving adapter 200. If driving adapter 200 is to be used with an implant 100 having a blade portion 104 that extends at an angle with respect to an axis defined by elongate threaded portion 102 such as the implant illustrated in FIGS. 5 and 6, then slot 210 may extend from distal edges 212 at an angle with respect to an axis defined by the length of body 202 such that elongate threaded portion 102 of implant 100 is linearly aligned with body 202 of driving adapter 200 as shown in FIG. 11. For example, if blade portion 104 of implant 100 extends at a ten degree angle with respect to an axis defined by elongate threaded portion 102, then slot 210 of driving adapter 200 may extend at a ten degree angle with respect to a longitudinal axis defined by body 202 such that threaded portion 102 of implant 100 and body 202 of driving adapter 200 are substantially linearly aligned.

Figure 12B:
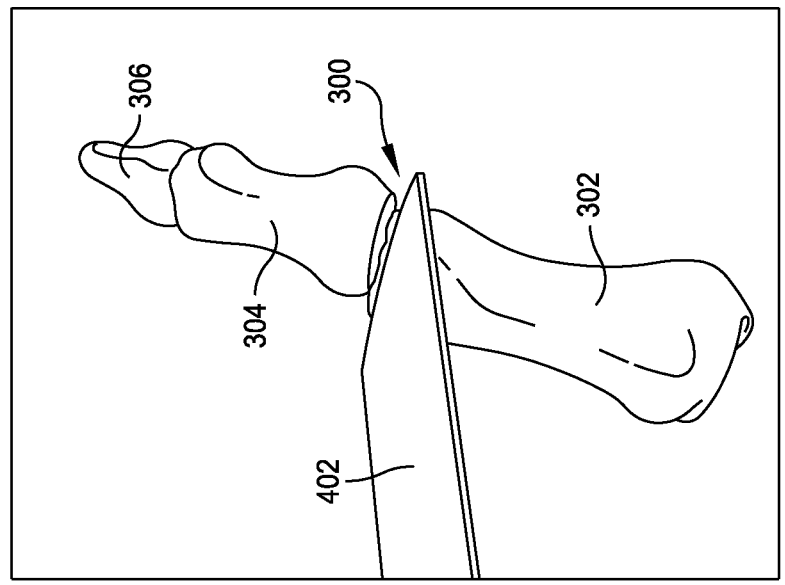
FIGS. 12A and 12B illustrate the middle and proximal phalanxes of a foot being resected.
Figure 12A:
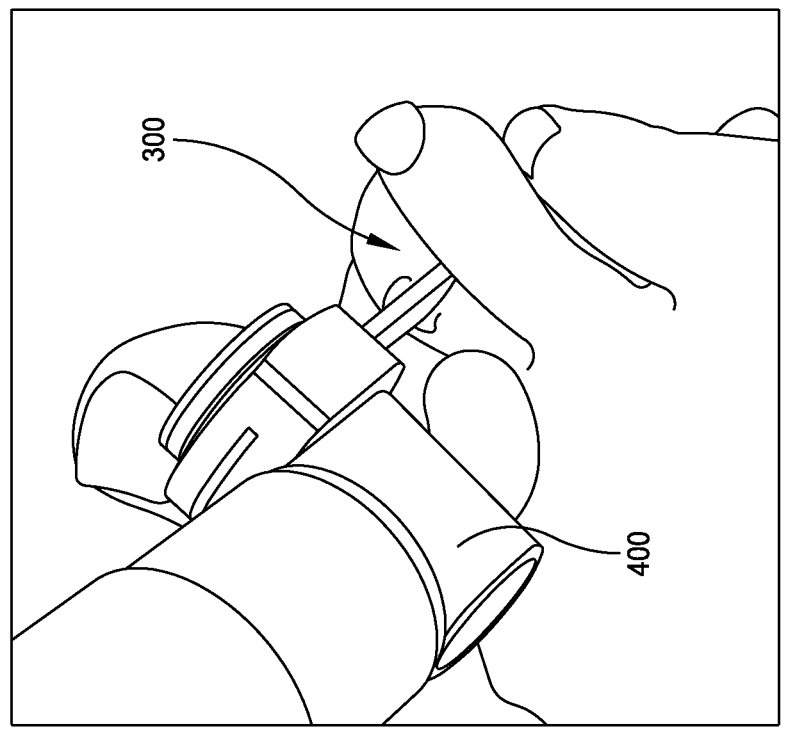

A method of installing implant 100 in the proximal interphelangeal joint (PIP) 300 is described with reference to FIGS. 12A-16. However, one skilled in the art will understand that the technique for installing the implant 100 may be applied to other joints such as, for example, the distal interphelangeal (DIP) joint between middle phalanx 304 and distal phalanx 306. As shown in FIGS. 12A and 12B, an incision is made to open the PIP joint 300 and a cutting tool 400 having a blade 402 may be used to resect adjacent faces of proximal phalanx 302 and middle phalanx 304. The resected surfaces of proximal phalanx 302 and middle phalanx 304 may be debrided as understood by one skilled in the art.

Figure 13:
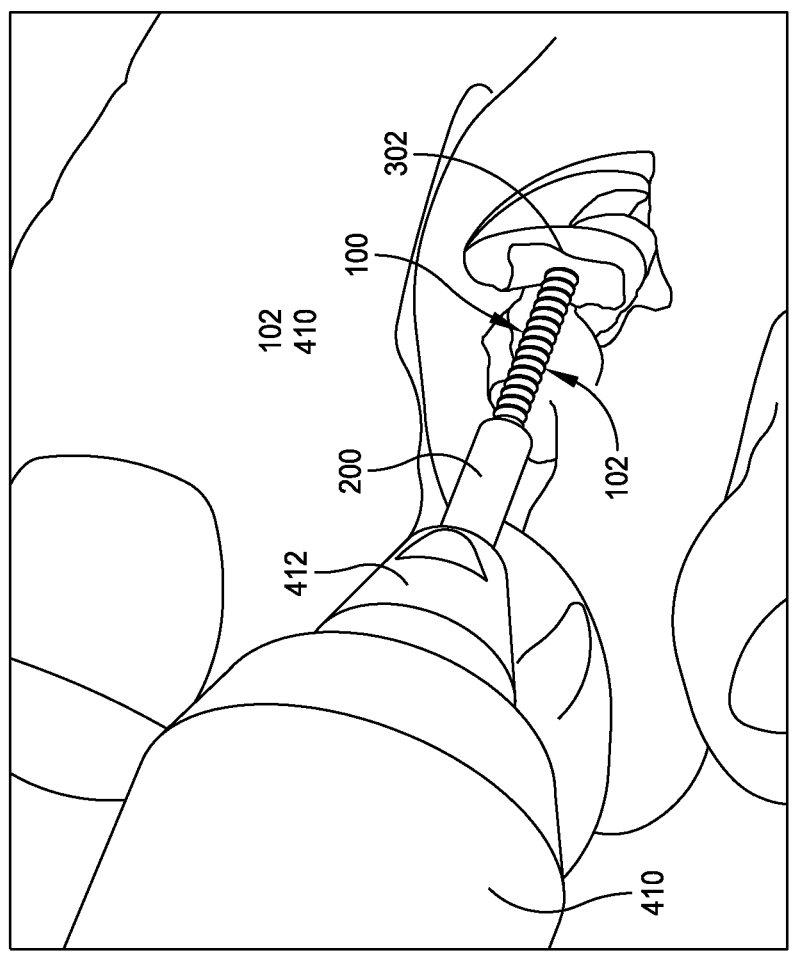
FIG. 13 illustrates a hammer toe implant being driven into a proximal phalanx.

Blade portion 104 of implant 100 may be disposed within slot 210 of driving adapter 200 as shown in FIG. 11, and the body 202 of driving adapter 200 may be secured in a chuck 412 of a drill 410 or other driving instrument as shown in FIG. 13. Drill 410 or other driving instrument is used to drive the threaded portion 102 of implant 100 into the resected surface of proximal phalanx 302. With the threaded portion 102 of implant 100 disposed within proximal phalanx 302, driving adapter 200 may be disengaged from blade portion 104 of implant 100.

Figure 14:
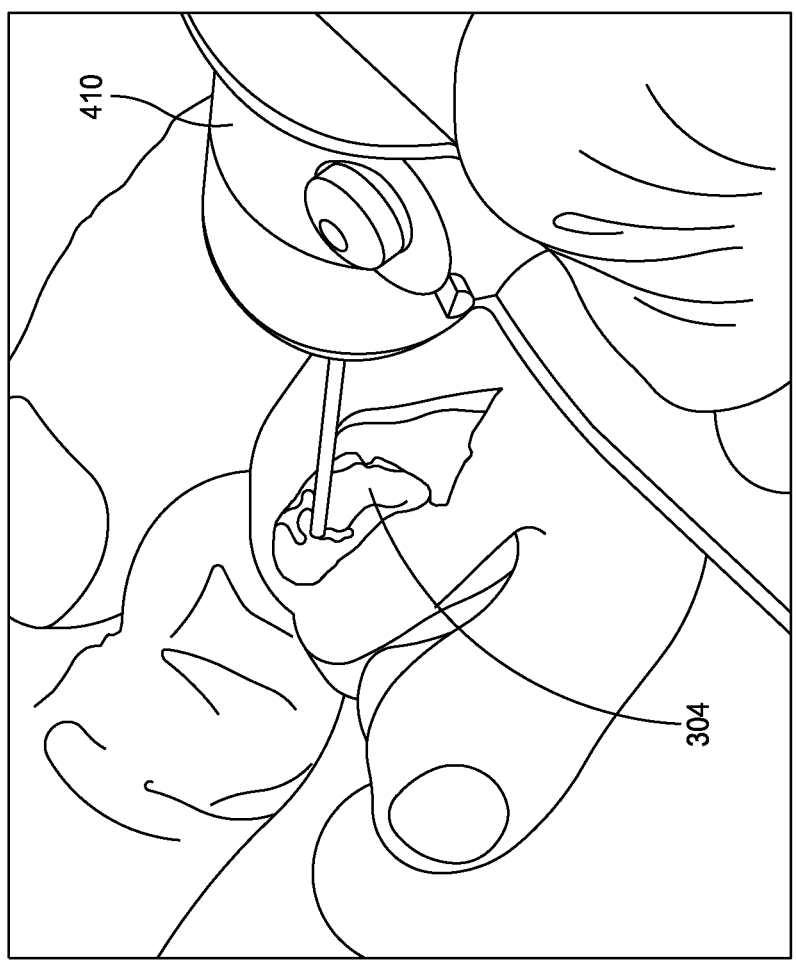
FIG. 14 illustrates a middle phalanx being drilled or broached.
Figure 15:
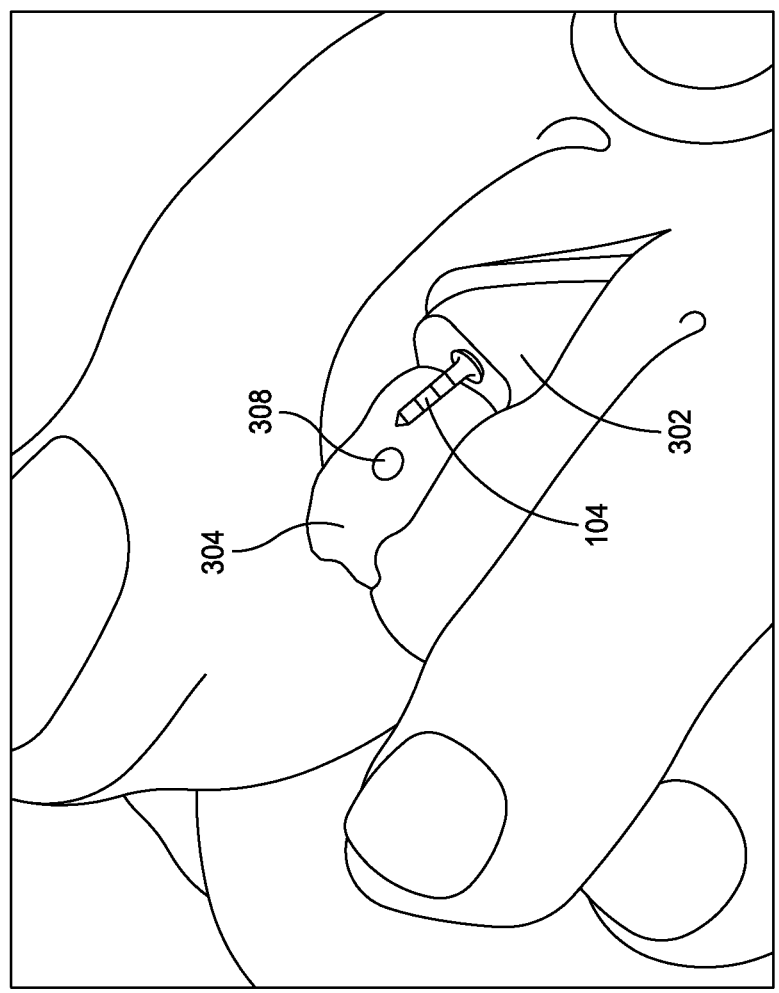
FIG. 15 illustrates a blade of a hammer toe implant extending from the proximal phalanx with the middle phalanx having been drilled or broached.
Figure 16:
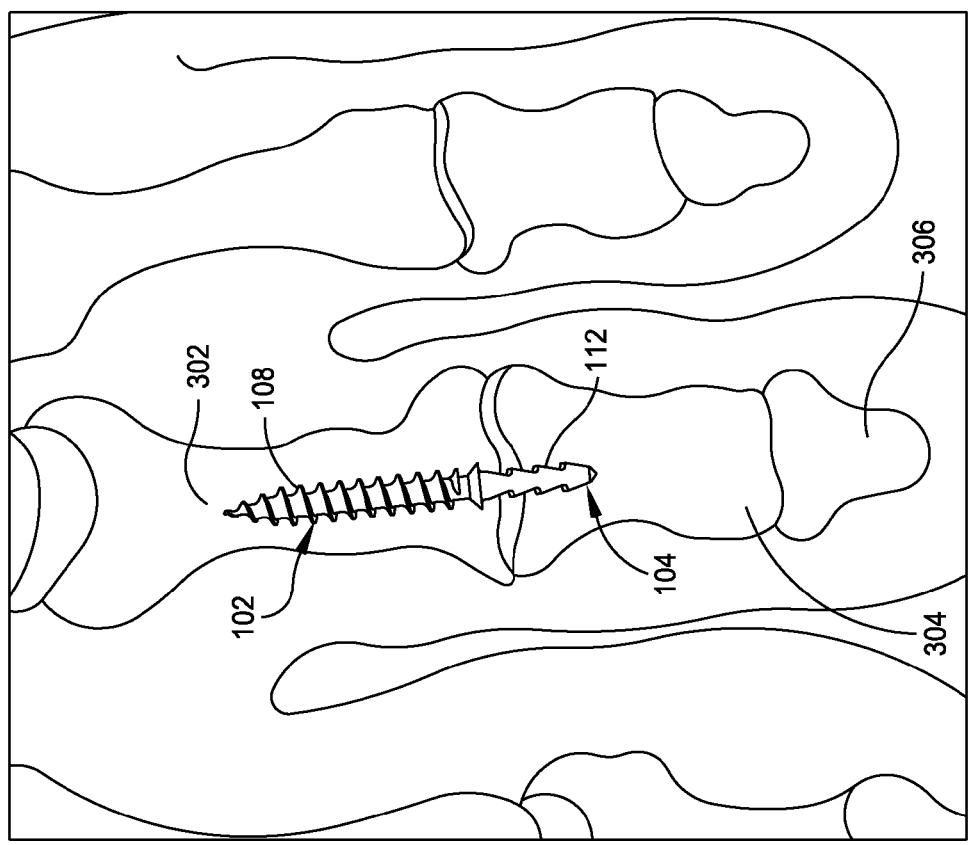
FIG. 16 illustrates a hammer toe implant installed in the middle and proximal phalanxes.

Middle phalanx 304 may be predrilled or broached using drill 410 to create a hole 308 as shown in FIGS. 14 and 15. The predrilled or broached middle phalanx 304 is then repositioned such that the predrilled hole or broach 308 aligns with the blade portion 104 of implant 100. The middle phalanx 304 is then pressed into engagement with the blade portion 104 as shown in FIG. 16. Serrated edges 112 of blade portion 104 help to maintain the engagement between middle phalanx 304 and blade portion 104 of implant 100.

Figure 17:
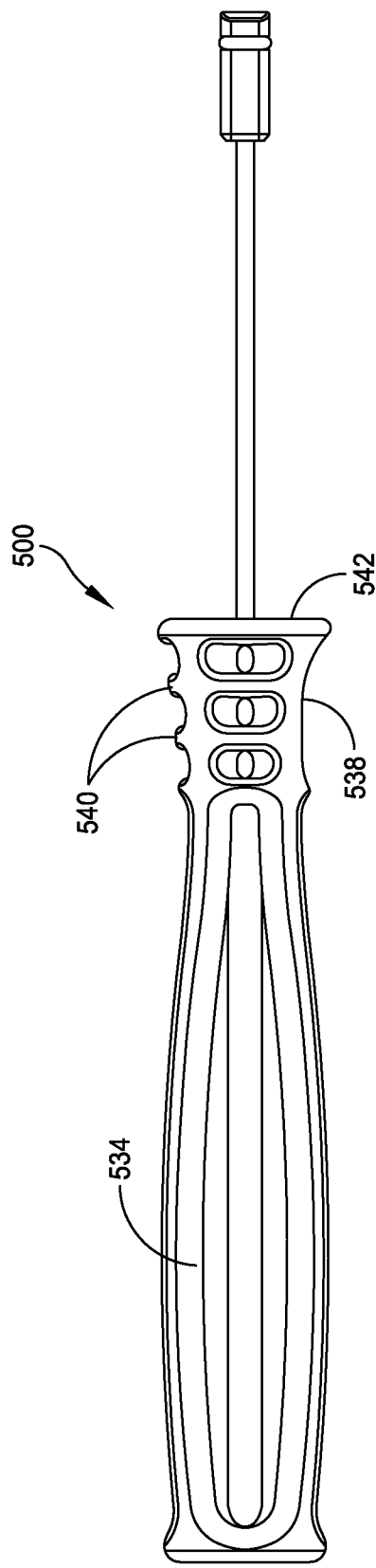
FIG. 17 illustrates another example of a driving assembly for installing an implant.
Figure 18:
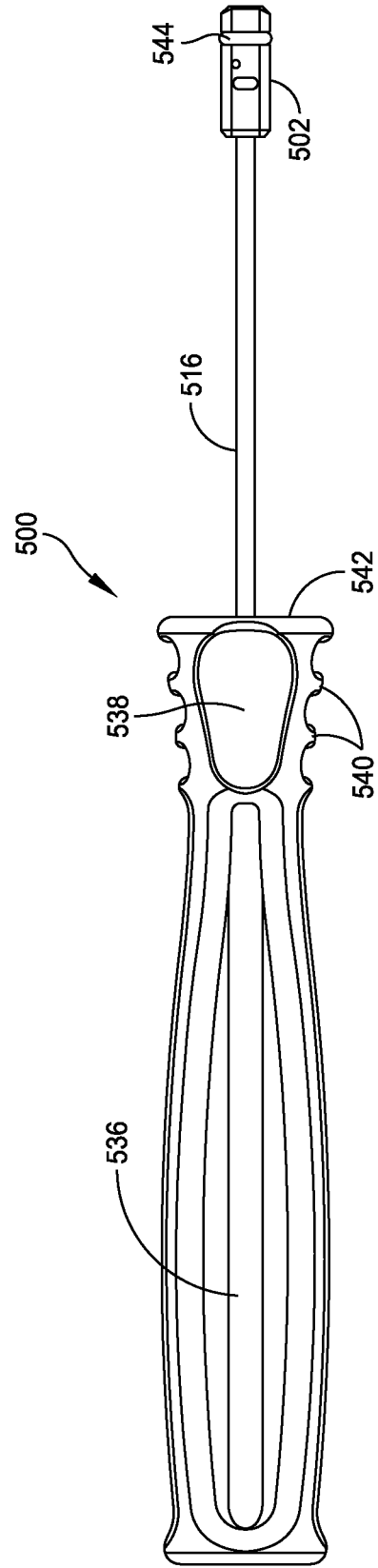
FIG. 18 illustrates side view of the driving assembly illustrated in FIG. 17.
Figure 20:
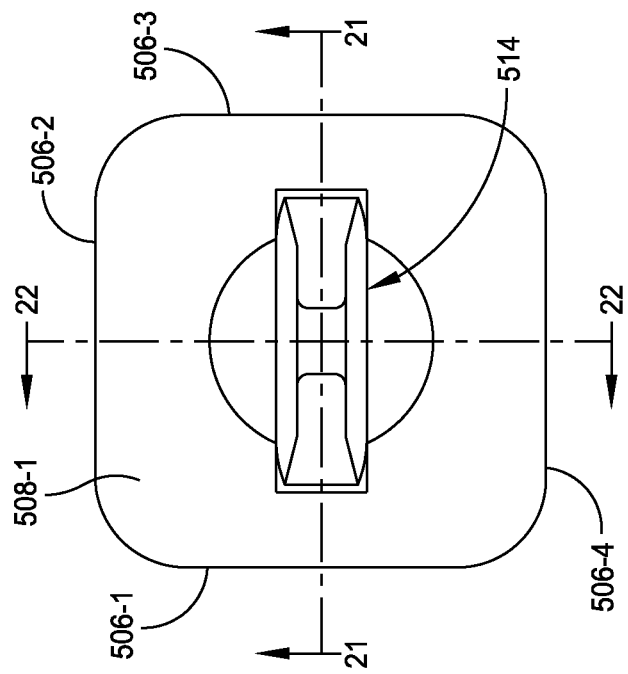
FIG. 20 is an end view of the adapter illustrated in FIG. 19.
Figure 19:
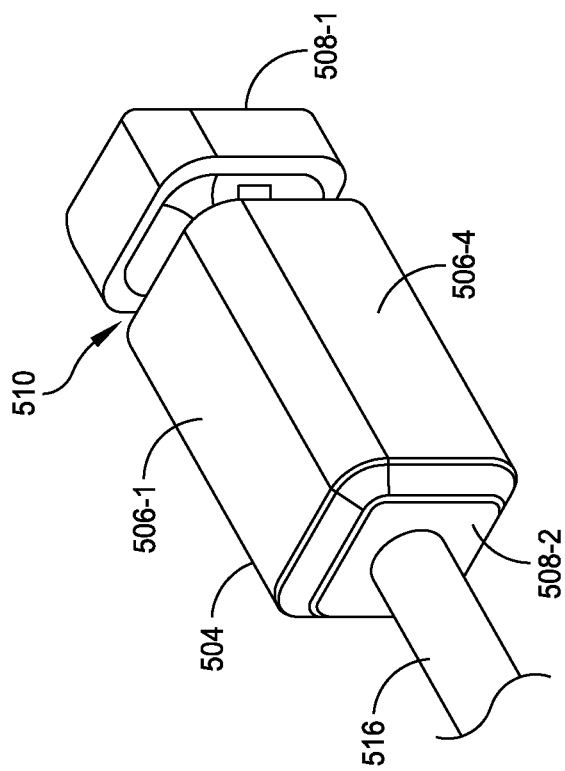
FIG. 19 is an isometric view of an adapter of the driving assembly illustrated in FIG. 17.

FIGS. 17-27 illustrate another embodiment of a driver assembly 500 for installing an implant into bone. As shown in FIGS. 17 and 18, driver assembly 500 includes an adapter 502 coupled to a driving rod 516 onto which a handle 534 is over-molded or otherwise coupled. Adapter 502 includes a body 504 with a substantially rectangular side profile comprising side walls 506-1, 506-2, 506-3, and 506-4 (collectively referred to as "side walls 506") and a pair of end walls 508-1, 508-2 (collectively referred to as "end walls 508") having a substantially square geometry as best seen in FIGS. 19-22.

Body 504 defines a recess 510 along the length of side walls 506. Recess 510 is dimensioned such that an o-ring 544 (FIGS. 17 and 18) may be received therein. Additionally, recess 510 is located along side walls 506 at a distance from end walls 508 such that recess 510 is aligned with a valley 126 of serrated edges 112 along the top and bottom sides 114, 116 of blade portion 104.

End wall 508-1 defines an aperture 512 having a geometry that complements the cross-sectional geometry of blade portion 104 of implant 100. For example, if implant 100 has a straight blade portion 104 as illustrated in FIG. 2, then aperture 512 may extend approximately parallel to the lengthwise direction of side walls 506. If the blade portion 104 of implant 100 is angled as illustrated in FIG. 6, then aperture 512 may extend from wall 508-1 at an angle relative to the plane defined by side wall 506-2 or 506-4 as will be understood by one skilled in the art. In some embodiments, aperture 512 has a depth that is greater than or equal to a length of blade portion 104 such that blade portion 104 may be received within body 504 and engagement portion 106 abuts end wall 508-1. Similarly, end wall 508-2 defines an aperture 514 that is sized and configured to receive an end of elongate driving rod 516 therein.

As best seen in FIGS. 23-25, driving rod 516 includes a fin 518 disposed at a first end 520. Fin 518 disposed at end 20 of driving rod 516 has a rectangular shape and is sized and configured to be received within aperture 512 of adapter 502. Fin 518 defines a slot 522, which is sized and configured to receive a pin (not shown) for cross-pinning driving rod 516 to adapter 502. In some embodiments, end 520 may have other cross-sectional geometries including, but not limited to, triangular, square, and pentagonal, to name a few possibilities, that are configured to be received within aperture 512. Adapter 502 may be over-molded onto the end of driving rod 516. However, one skilled in the art will understand that adapter 502 may be cross-pinned or otherwise coupled to driving rod 516.

The opposite end 524 of driving rod 516 defines a pair of flats 526, 528, which are disposed on opposite sides of driving rod 516. As best seen in FIG. 23, flat 526 extends from tip 530 and is linearly spaced from flat 528, which is disposed at a greater distance from tip 530 than flat 526. However, one skilled in the art will understand that flats 526, 528 may be disposed at other positions along driving rod 516. Flats 526, 528 are configured to provide a contact surface for coupling to handle 532, which may be over-molded onto driving rod 516, such that rotation of handle 532 is translated to driving rod 516.

Figure 22:
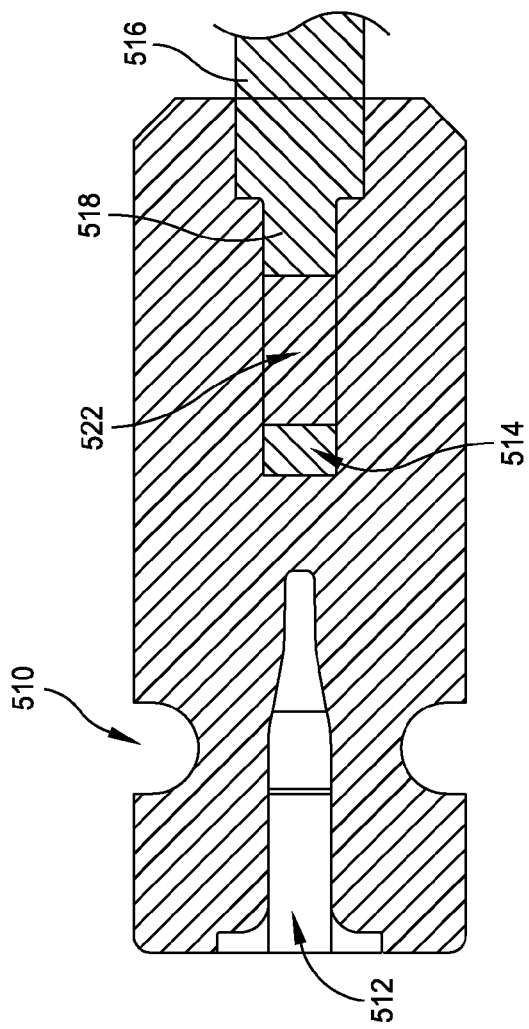
FIG. 22 is a cross-sectional view of the adapter taken along line 22-22 in FIG. 20.
Figure 21:
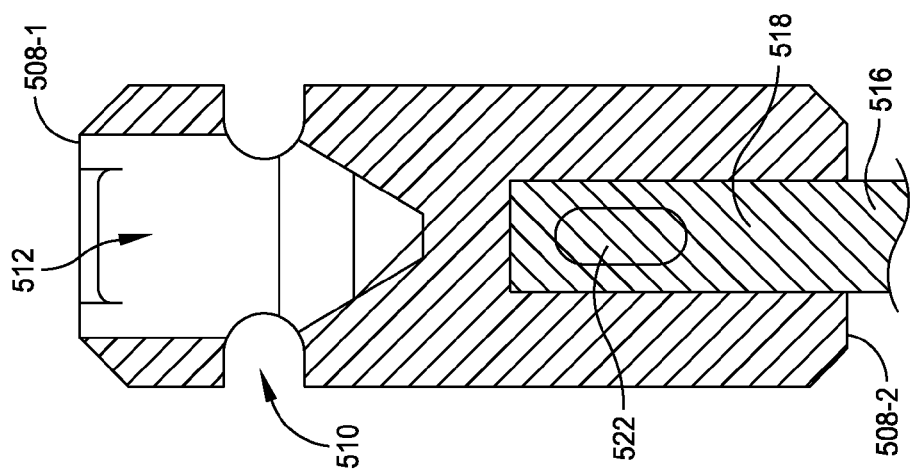
FIG. 21 is a cross-sectional view of the adapter taken along line 21-21 in FIG. 20.
Figure 26:
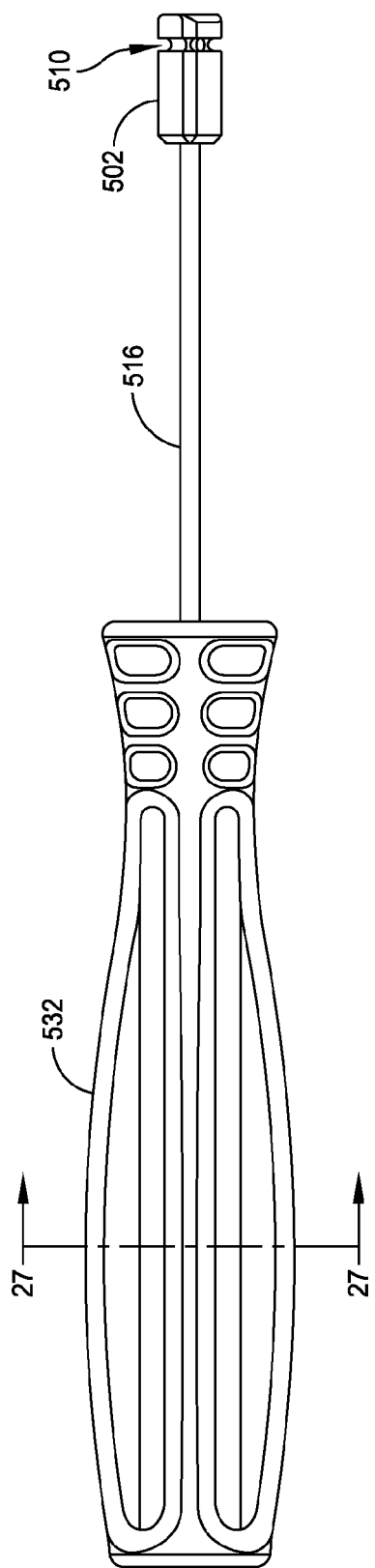
FIG. 26 is a plan view of driving assembly illustrated in FIG. 17 without the o-ring.
Figure 27:
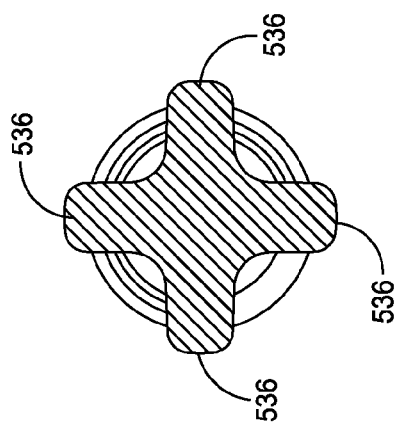
FIG. 27 is a cross-sectional view of the handle taken along line 27-27 in FIG. 26.

Turning now to FIGS. 26 and 27, handle 532 has an elongate body 534 that includes a plurality of ribs 536 that extend in a longitudinal direction along body 534 to provide a gripping surface for a user. As best seen in FIGS. 17 and 22, a smooth surface 538 interrupts circumferential ridges 540, which are disposed adjacent to proximal end 542 also for providing a gripping surface for a user.

Driver assembly 500 may be provided in a kit with a first adapter 502 for use with a straight implant 100 and a second adapter for use with an angled implant 100. A plurality of implants 100 of different sizes may also be provided in the kit. The kit may be used in an operation similar to the operation described above with respect to FIGS. 12A-16.

Figure 28B:
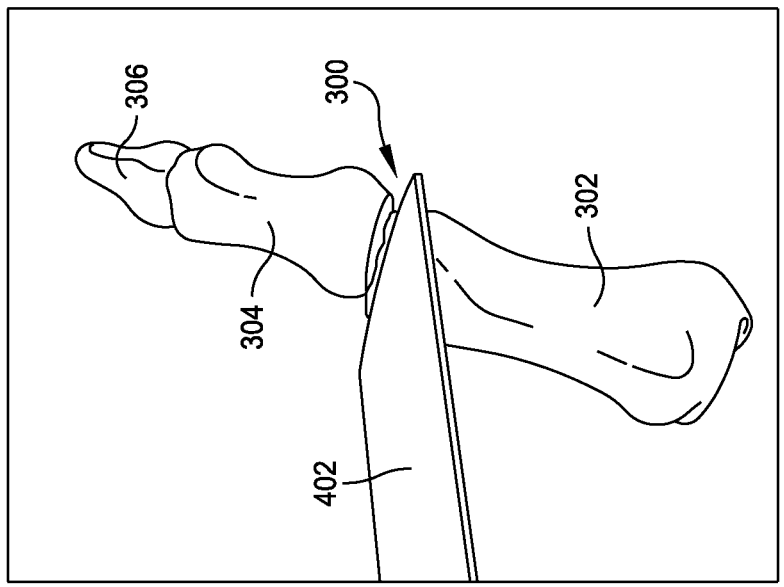
FIGS. 28A and 28B illustrate the middle and proximal phalanxes of a foot being resected.
Figure 28A:
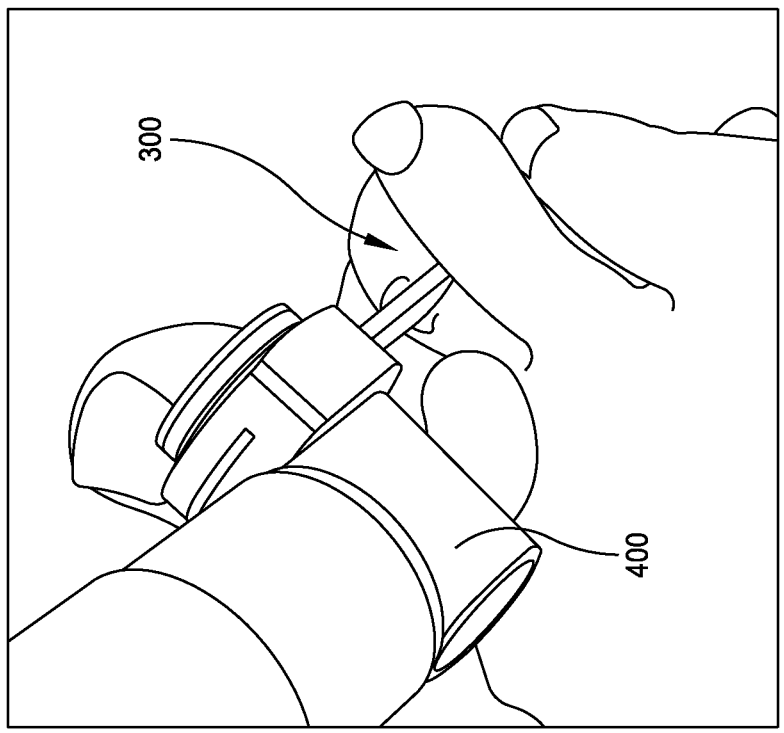

For example and referring to FIGS. 28A-33, an incision is made to open the PIP joint 300 and a cutting tool 400 having a blade 402 may be used to resect adjacent faces of proximal phalanx 302 and middle phalanx 304 as illustrated in FIGS. 28A and 28B. The resected surfaces of proximal phalanx 302 and middle phalanx 304 may be debrided as understood by one skilled in the art.

Figure 29A:
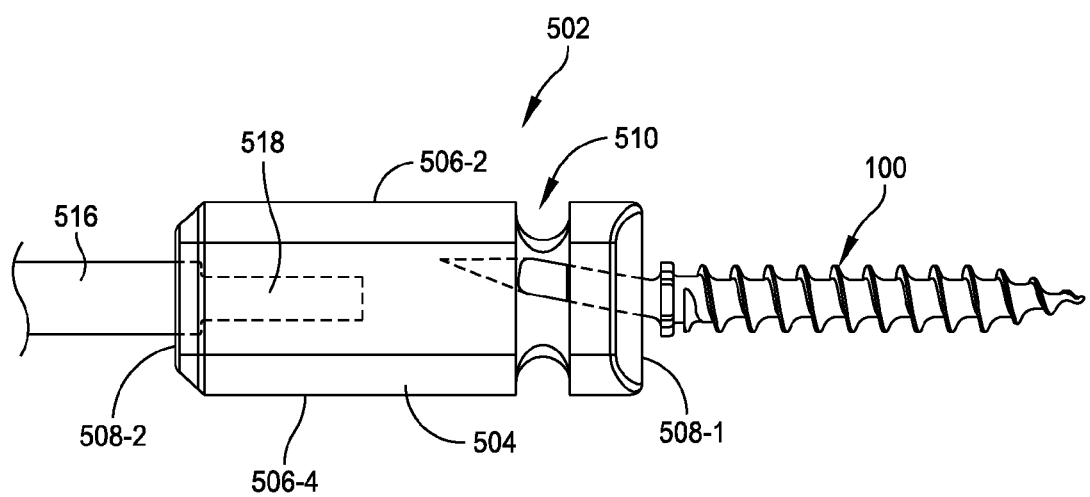
FIGS. 29A and 29B illustrate an implant coupled to the adapter of the driving assembly illustrated in FIG. 17.
Figure 29B:
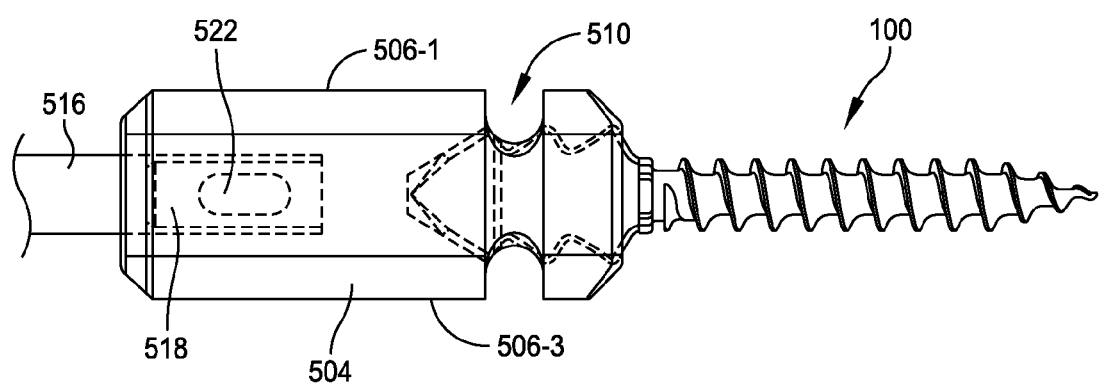

Blade portion 104 of implant 100 is disposed within aperture 512 of adapter 502 as shown in FIGS. 29A and 29B. With blade portion 104 disposed within aperture 512, an o-ring 544 (FIGS. 17 and 18) is placed in recess 510 defined by adapter 502 and within a valley 126 of serrated edges 112 along the top and bottom sides 114, 116 of blade portion 104. O-ring 544 secures implant 100 to adapter 502 such that implant does not move axially out of aperture 512.

Figure 30:
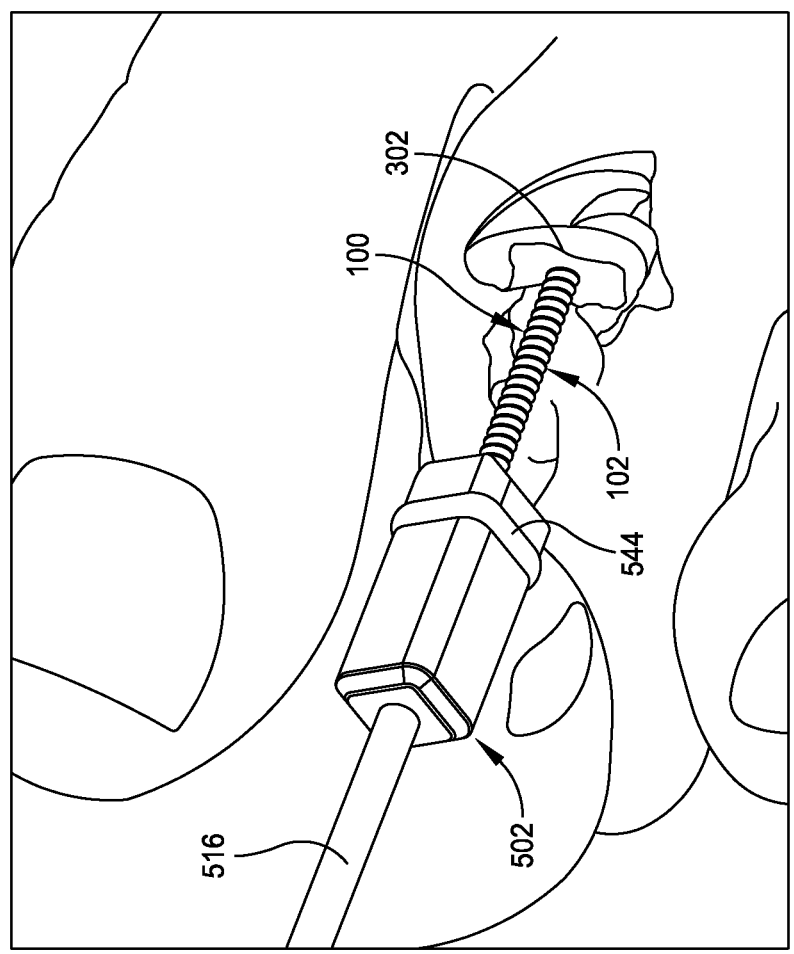
FIG. 30 illustrates a hammer toe implant being driven into a proximal phalanx.

Once implant 100 is secured to adapter 502, the surgeon uses handle 534 to manually drive threaded portion 102 of implant 100 into the resected surface of proximal phalanx 302 as illustrated in FIG. 30. Implant 100 is driven into proximal phalanx 302 until engagement portion 106 abuts proximal phalanx 302. Implant 100 is decoupled from adapter 502 by axially pulling handle 534 away from implant 100 with sufficient force to flex o-ring 544 and separate adapter 502 from implant 100.

Figure 31:
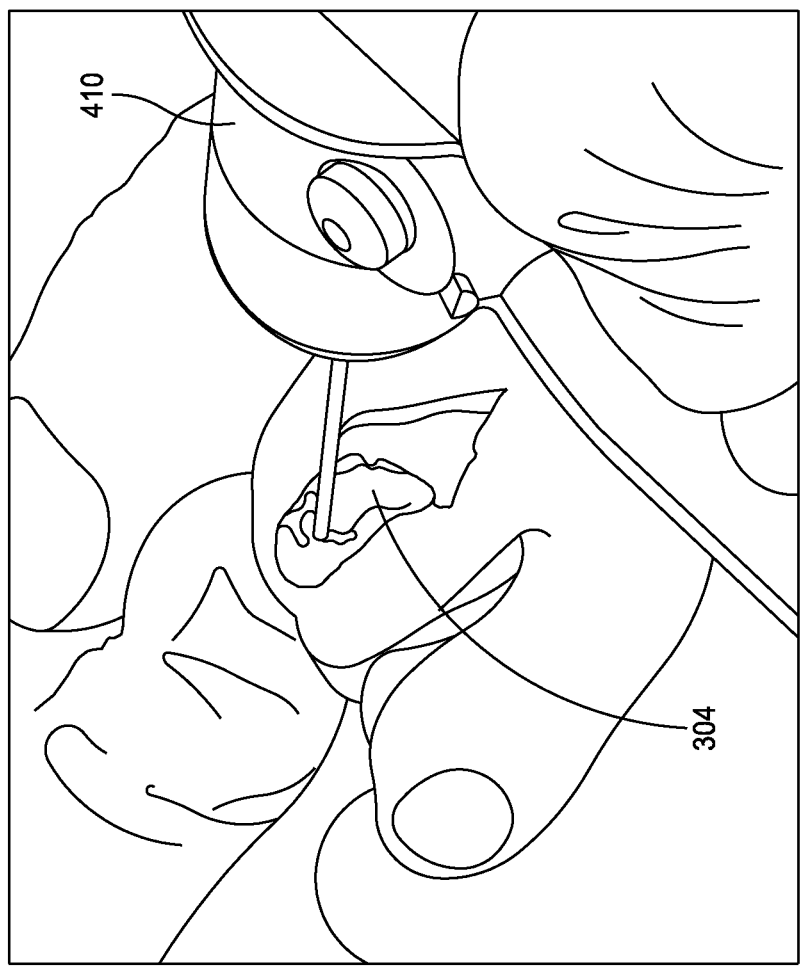
FIG. 31 illustrates a middle phalanx being drilled or broached.
Figure 32:
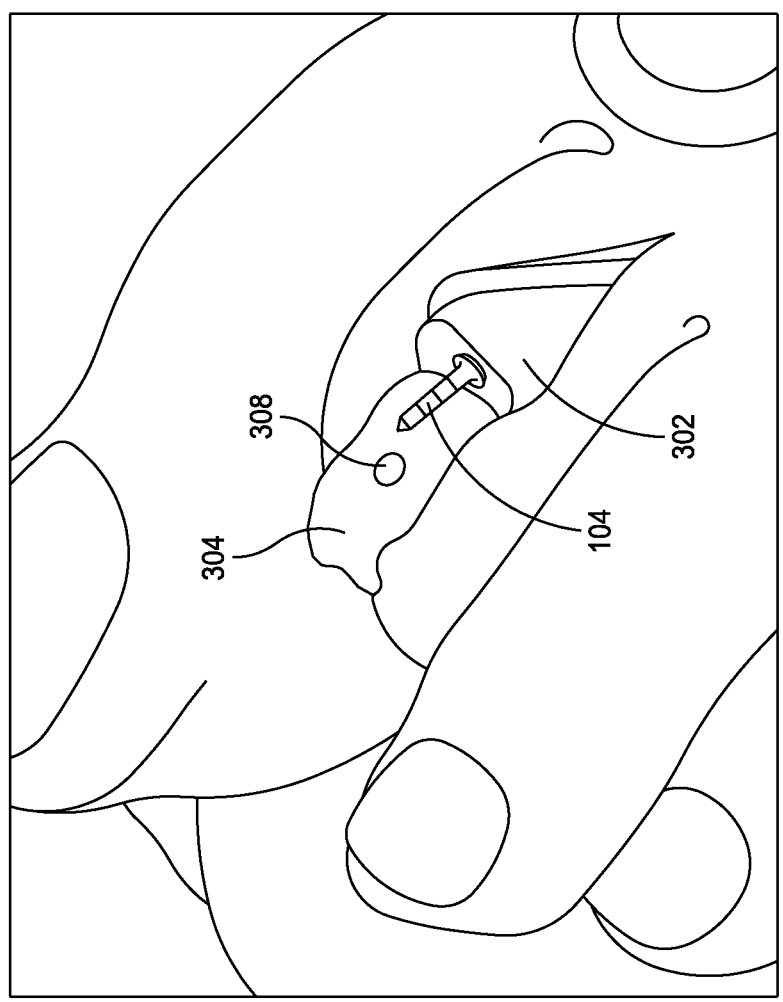
FIG. 32 illustrates a blade of a hammer toe implant extending from the proximal phalanx with the middle phalanx having been drilled or broached.
Figure 33:
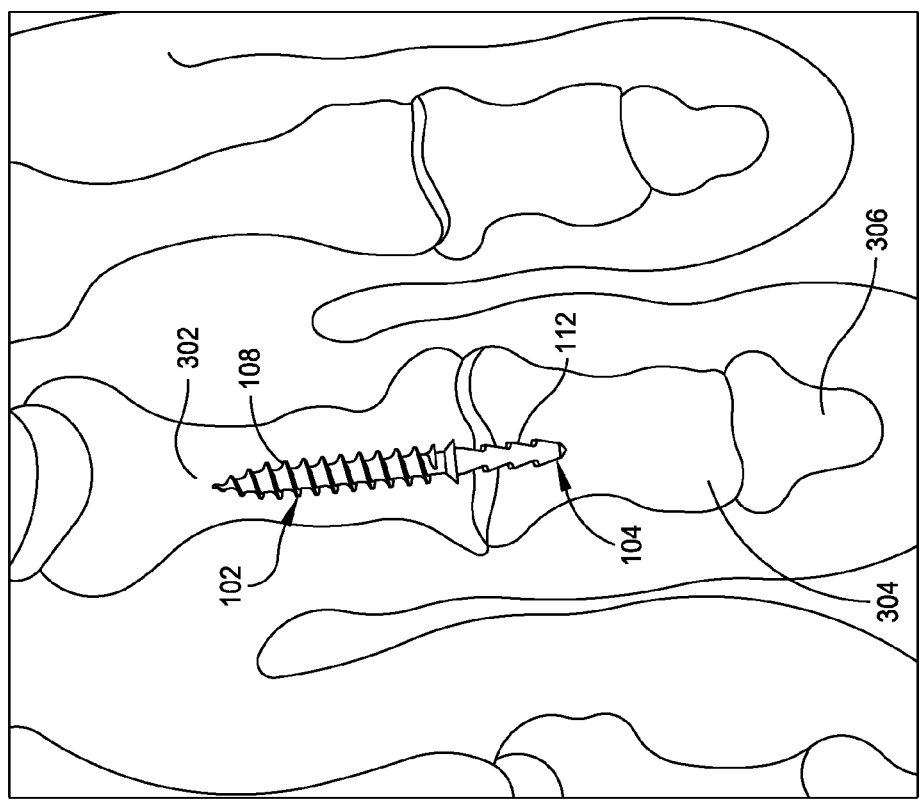
FIG. 33 illustrates a hammer toe implant installed in the middle and proximal phalanxes.

Middle phalanx 304 may be predrilled or broached using drill 410 to create a hole 308 as shown in FIGS. 31 and 32. The predrilled or broached middle phalanx 304 is then repositioned such that the predrilled hole or broach 308 aligns with the blade portion 104 of implant 100. The middle phalanx 304 is then pressed into engagement with the blade portion 104 as shown in FIG. 33. Serrated edges 112 of blade portion 104 help to maintain the engagement between middle phalanx 304 and blade portion 104 of implant 100.

The implant described above may advantageously be installed through a small incision as described above. Additionally, the improved implant is completely disposed within a toe of a patient, which prevents the implant from being caught on bed sheets or other objects like the conventional pins.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. An implant, comprising:
    an elongated threaded portion;
    a blade portion extending from the elongate threaded portion, the blade portion having a taper terminating at a point disposed at an end of the blade portion, wherein the blade portion includes a plurality of serrated edges and two flat surfaces positioned between the serrated edges; and
    an engagement portion disposed between the elongated threaded portion and the blade portion, the engagement portion including first and second protrusions that extend in opposite directions from one another, the first and second protrusions in direct contact with the two flat surfaces of the blade and extending from the respective flat surfaces of the blade portion such that both engagement portions extend a direction away from a longitudinal axis defined by the elongate threaded portion, each of the first and second protrusions including a pair of parallel sides between which sides is a side with a rounded outer edge, said opposite directions normal to a width of the blade portion.

2. The implant of claim 1, wherein the blade portion tapers along width and thickness to the point.

3. The implant of claim 1, wherein the direction in which the first and second protrusions extend away from the longitudinal axis defined by the elongate threaded portion is approximately perpendicular to the longitudinal axis defined by the threaded portion.

4. The implant of claim 1, wherein the blade portion extends from the elongated threaded member at angle between, but not including, zero and 45 degrees with respect to the longitudinal axis defined by the elongate threaded member.

5. The implant of claim 4, wherein the angle is between five and 15 degrees.

6. The implant of claim 1, wherein the blade portion includes a rectangular cross-sectional geometry with a width dimension being greater than a thickness dimension, and a plurality of serrated edges disposed along opposed sides of the blade portion and each defining a flat extending perpendicular to the longitudinal axis.

7. The implant of claim 1, wherein the blade portion is symmetric with respect to a plane which includes the axis defined by the threaded portion; and, the point lies within the plane, said plane normal to the width of the blade portion.

8. The implant of claim 7, wherein the plane bi-sects the flats of the blade portion.

9. The implant of claim 1, wherein the width of the protrusions is less than the width of the blade portion proximate the protrusion.

10. The implant of claim 1, wherein the width of the blade portion along the entire length of the blade portion is greater than the respective thickness of the blade portion.

11. An implant, comprising:
    an elongated threaded portion extending in a first direction away from an engagement portion and defining a longitudinal axis; and
    a blade portion extending from the engagement portion in a second direction and terminating at a point at an end of the blade portion,
    wherein the blade portion includes a rectangular cross-sectional geometry with a width dimension being greater than a thickness dimension, and
    a plurality of serrated edges disposed along opposed sides of the blade portion and each defining a flat extending perpendicular to the longitudinal axis, wherein the engagement portion includes first and second protrusions that extend in opposite directions from one another and are in direct contact with the flats and extend from the respective flats of the blade portion such that both engagement portions extend in a direction away from a longitudinal axis defined by the threaded portion, said opposite directions normal to a width of the blade portion.

12. The implant of claim 11, wherein the first and second protrusions extend in opposite directions from one another and both extend in a direction away from the longitudinal axis, each of the first and second protrusions including a pair of parallel sides between which sides is a side with a rounded outer edge.

13. The implant of claim 12, wherein the second direction being disposed at angle between five and 15 degrees relative to the longitudinal axis.

14. The implant of claim 13, wherein the blade portion tapers along width and thickness to the point.

15. The implant of claim 11, wherein the blade portion is symmetric with respect to a plane which includes the axis defined by the threaded portion; and, the point lies within the plane.

16. The implant of claim 15, wherein the plane bi-sects the flats of the blade portion.

17. The implant of claim 11, wherein the spacing between one of the pair of parallel sides and the other of the pair of parallel sides is less than the width of the blade portion proximate the protrusion.

18. The implant of claim 11, wherein the width of the blade portion along the entire length of the blade portion is greater than the respective thickness of the blade portion.

19. An implant, comprising:
    a self-tapping threaded portion extending along a longitudinal axis and having a length greater than its diameter;
    a blade portion extending from the threaded portion, the blade portion having a width and corresponding thickness along its length and a taper terminating at a point disposed at an end of the blade portion, the blade portion having opposing flat surfaces bounded by a plurality of serrated edges, a distance between the opposing surfaces corresponding to the thickness;
    an engagement portion disposed between the threaded portion and the blade portion, the engagement portion including first and second protrusions that extend in opposite directions from one another and are in direct contact with the flat surfaces and extend from respective opposing flat surfaces of the blade portion such that both engagement portions extend a direction away from a longitudinal axis, each of the first and second protrusions including a pair of parallel sides between which is a side with a rounded outer edge, said opposite directions normal to the width of the blade portion, wherein a width of each protrusion is less than the width of the blade portion proximate the protrusion.

20. The implant of claim 19, wherein the width of the blade portion along the entire length of the blade portion is greater than the respective thickness of the blade portion.

21. The implant of claim 19, wherein the spacing between one of the pair of parallel sides and the other of the pair of parallel sides is less than the width of the blade portion proximate the protrusion.

22. The implant of claim 19, wherein the rounded outer edge is bounded by the plane defining each of the parallel sides and terminates at an end of each of the parallel sides.

* * * * *